United States Patent [19]

Guth

[11] 4,263,178

[45] Apr. 21, 1981

[54] HAIR SHAMPOO COMPOSITION

[75] Inventor: Jacob J. Guth, Upper Black Eddy, Pa.

[73] Assignee: The Gillette Company, Boston, Mass.

[21] Appl. No.: 97,291

[22] Filed: Nov. 29, 1979

[51] Int. Cl.³ .................... C11D 1/75; C11D 3/26; C11D 7/32

[52] U.S. Cl. .................... 252/547; 252/549; 252/550; 252/DIG. 13; 132/7; 424/70; 252/174.19

[58] Field of Search .......... 252/549, 550, 547, 179.19, 252/DIG. 13; 424/70; 132/7

[56] References Cited

U.S. PATENT DOCUMENTS 4,064,076  12/1977  Klisch et al. .................... 252/550 X

*Primary Examiner*—Mayer Weinblatt
*Attorney, Agent, or Firm*—Richard A. Wise; Leonard J. Janowski

[57] ABSTRACT

This invention deals with novel hair shampoo compositions containing sulfated alkoxylated polyglycerol surfactants in combination with alkyl amine oxide foam promoters. The shampoo compositions have unusually low levels of skin and eye irritation.

6 Claims, No Drawings

HAIR SHAMPOO COMPOSITION

FIELD OF THE INVENTION

This invention deals with novel hair shampoo compositions containing sulfated alkoxylated polyglycerol surfactants in combination with alkyl amine oxide foam promoters. The shampoo compositions have unusually low levels of skin and eye irritation.

PRIOR ART

A variety of polyglycerol-derived surfactants have been reported in the literature as being useful in the formulation of hair shampoos and other personal care cleansing compositions. Among these in U.S. Pat. No. 3,932,532 which discloses a method of preparing homogeneous, light colored ether derivatives of polyglycerols. These materials are said to be useful as surfactants having improved hydrolytic stability and especially useful in cosmetic applications.

A variety of cationic polyglycerol derivatives said to be useful as low foaming surfactants are described in German Pat. Nos. 2,732,100 and 2,732,178.

To the best of our knowledge, however, nowhere in the prior art is it suggested that sulfated alkoxylated polyglycerol surfactants as will be more fully described hereinafter be combined with alkyl amine oxide foam promoters to yield a cosmetically useful anionic shampoo compositions having unusually low levels of skin and eye irritation.

SUMMARY OF THE INVENTION

The sulfated alkoxylated polyglycerols used as a component in the compositions of this invention are prepared by reacting a purified polyglycerol with alpha olefin epoxide of the general formula

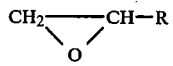

where R is $C_8$ to $C_{16}$ alkyl, in the presence of an alkali metal alkoxide catalyst. The resulting ether is then sulfated by reaction with a sulfating agent such as chlorosulfonic acid and converted to an alkali metal salt by pouring the reaction mixture into an equivalent amount of stirred aqueous alkali metal hydroxide after which the pH adjusted to 8 to 9. The sulfated alkoxylated polyglycerol is then formulated with an alkyl amine oxide foam promoter to yield a hair shampoo composition.

DESCRIPTION OF THE PREFERRED EMBODIMENTS

In accordance with the present invention alkyl ethers of polyglycerols are first prepared by reacting in the presence of an alkali metal alkoxide catalyst a purified polyglycerol and an alpha olefin epoxide. Although polyglycerols having 2 to 15 glycerol units may be utilized, preferred results have been achieved with materials containing from about 3 to 8 units. Especially preferred results have been achieved with the material containing six glycerol units i.e. hexaglycerol.

The alpha olefin epoxide which is reacted with the purified glycerol to prepare the alkyl ethers as the first step in the practice of the present invention is selected from the compounds of the general formula

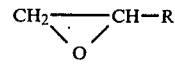

where R is an alkyl group containing from about 8 to 16 carbon atoms. It has been found that when epoxides with alkyl substituents having less than about 8 carbon atoms are employed, the resulting products are too hydrophilic to be useful as surfactants. Also if epoxides with alkyl substituents having more than about 16 carbon atoms are employed, the resulting products are too hydrophobic to be useful. The alpha olefin epoxides may be utilized either as individual compounds or as mixtures of two or more of the above-identified materials.

To produce the polyglycerol ethers as the first step of the present invention, the amount of epoxide employed should be equal to at least 0.25 mole per mole of glycerol contained in the polyglycerol. Additional epoxide may be employed depending upon the desired properties of the resulting product. In general, as the amount of any given epoxide is increased, the product becomes more hydrophobic for a given level of sulfation.

In reacting the purified polyglycerol with the alpha olefin epoxide as described above, it has been found to be essential to employ as a catalyst for the reaction an alkali metal alkoxide. This catalyst may be prepared by reacting an alkali metal with a hydroxyl-containing compound, such as methanol, ethanol, butanol or the like and adding the resulting alkali metal alkoxide to the purified polyglycerol prior to the addition of the alpha olefin epoxide. Alternatively, the catalyst may be prepared in situ by adding the alkali metal directly to the reaction mixture resulting in the formation of an alkoxide of the polyglycerol.

The amount of catalyst employed is preferably equal from about 0.1% to 3.0% by weight based on the weight of the polyglycerol in the reaction mixture. If less than 0.1% catalyst is employed, the reaction is too slow to be practical as a commercial operation. Also if more than about 3.0% catalyst is used, no further increase in reaction rate is noted and undesirable side reactions may ensue.

Since the etherification reaction of the present invention is carried out under anhydrous conditions, it is therefore necessary to dry the polyglycerol employed. This may be done, for example, by vacuum stripping the material to a temperature of about 125° C. at a pressure of about 0.35 mm Hg. Following the addition of the catalyst, the mixture may be again stripped to remove any alcohol formed from the reaction of the catalyst with the polyglycerol. The alpha olefin epoxide is then added.

The resulting reaction mixture is then heated preferably under a nitrogen atmosphere to an elevated temperature to increase the rate of the reaction. The actual temperature employed is not narrowly critical to the present invention and only affects the reaction rate. However, it has been found the preferred results are achieved if the reaction is carried out at temperatures in the range of from about 130° to 170° C. It is especially preferred to carry out the reaction at a temperature of about 160° C. The reaction mixture is heated at this temperature with vigorous stirring for five or six hours or until no unreacted epoxide can be detected by titration with pyridine hydrochloride. The resulting products may be either monoethers or higher ethers depending upon the amount of alpha olefin epoxide employed in the reaction mixture.

Partial or complete sulfation of the hydroxyl groups present in the polymers produced above may be accomplished through the use of conventional sulfating agents such as those used in the sulfation of fatty alcohol sulfates and their alkoxylated derivatives. These include the various known complexes of sulfur trioxide such as the complexes with dioxane, triethylamine, ammonia and hydrochloric acid. We prefer to sulfate by the slow addition of a hydroxyl equivalent of chlorosulfonic acid to a methylene chloride solution of the polymeric material. The level of sulfation is generally based on the level of alkoxylation of the polyglycerol. Although water dispersible, surface active sulfated alkoxylated polyglycerols are obtained over the range of 0.3 to 2.0 moles of sulfating agent per mole of alkoxide used to alkoxylate each mole of polyglycerol, preferred results have been obtained with materials within the range of 0.5 to 1.2. The stirred reaction solution is cooled to prevent the temperature from exceeding 25° C. Upon completion of the addition, the solution is sparged with nitrogen to remove any HCl which is present. The sulfuric acid ester is then converted to a salt by pouring the reaction mixture into an equivalent amount of stirred aqueous ammonia, amine or alkali earth metal hydroxide. The pH of the resulting emulsion is adjusted with additional aqueous alkali. The organic solvents are then removed by distillation to yield a concentrated aqueous solution of the sodium salt of the sulfated polymer. The ionic group of the surface active copolymers prepared as described above is the sulfate ion, the most hydrophilic of the anionic functional groups. It is especially useful in the formation of personal care compositions because of its minimal tendencies to complex with metal ions and its minimal sensitivity to hard water.

The sulfated alkoxylated polyglycerols prepared as described above all demonstrate sufficient detergent activity to be useful as cleansing surfactants in personal care applications. However, their foaming properties had been found to be unacceptable for many such applications. We have found that it is accordingly necessary to formulate these surfactants along with low irritating foam promoters taken from the group consisting of amine oxides of the general formula

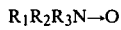

The arrow is a conventional representation of a semipolar bond. These compounds are generally prepared by the direct oxidation of the appropriate tertiary amine. When $R_1$ is a much longer chain than $R_2$ and $R_3$, the amine oxides have surface activity. For the purpose of this invention $R_1$ is an alkyl group having from 10 to 16 carbon atoms. Desirable surface active properties are lost if $R_1$ is substantially less than 10 carbon atoms, and the compounds are insufficiently soluble if $R_1$ is greater than 16 carbon atoms. $R_2$ and $R_3$ are each selected from the group consisting of methyl and ethyl groups. Preferably $R_1$ is a dodecyl group or a mixture of dodecyl with decyl, tetradecyl and hexadecyl, such that at least 50% of the groups are dodecyl groups. $R_2$ and $R_3$ are preferably methyl groups. A preferred amine oxide for the purpose of this invention is dodecyldimethylamine oxide.

We have found unexpectedly that when these two classes of materials are combined in aqueous composition, not only are the foaming properties improved, but there is also an unexpected synergistic improvement in detergent properties. In formulating the compositions of this invention, the sulfated alkoxylated polyglycerol surfactant and amine oxide foam promoter may each comprise about 5% to about 20% by weight of the total composition. Preferably, each component will comprise from about 7% to about 15%. The aqueous vehicle may, in addition, include such materials as organic solvents, thickeners, perfumes, sequestering agents and opacifiers useful in enhancing the cosmetic properties of shampoo formulations.

EXAMPLE I

Preparation of Trisulfated Dialkoxylated Triglycerol (I)

a. Synthesis of Dialkoxylated Triglycerol (Ia)

To a three-necked flask equipped with stirrer, thermometer and nitrogen inlet tube was added 120 grams (1.0 mole) of triglycerol. Water was removed from the triglycerol by stirring at 150° C. under a vacuum of approximately 10 mm Hg. Five grams of 25% sodium methoxide in methanol was added, and the catalyzed triglycerol was again vacuum stripped. Then 247 grams (2.0 moles) of NEDOX 1518 (Ashland Chem. CO.), a mixed alpha olefin epoxide having an alkyl group containing from 13 to 16 carbons, was added. The reaction mixture was heated under a nitrogen atmosphere to 160° C. for 5 hours. Less than 1.0% epoxide was detected by titration with pyridine hydrochloride. The cooled product, a dialkoxylated triglycerol, was sulfated without further purification.

b. Trisulfation of Dialkoxylated Triglycerol

To a three-necked flask equipped with stirrer, thermometer, dropping funnel and reflux condenser was added 73.4 grams (0.20 mole) of the di-NEDOX 1518 adduct of triglycerol (Ia). Anhydrous methylene chloride (350 grams) was added to solubilize the triglycerol derivative. Chlorosulfonic acid (77.3 grams, 0.63 mole) was added to the dropping funnel. The acid was slowly added to the stirred solution, and cooling was applied to maintain a solution temperature less than 25° C. Upon completion of the addition, the solution was sparged with nitrogen to remove dissolved HCl. The sulfuric acid ester slution of Ia was then added to 25 grams of sodium hydroxide dissolved in 700 mL of water. Additional 10% aqueous sodium hydroxide was added to stabilize the pH at 8-9. The methylene chloride was then removed by distillation to yield an aqueous solution of compound I.

EXAMPLE II

Preparation of Monosulfated Dialkoxylated Hexaglycerol (II)

a. Synthesis of Dialkoxylated Hexaglycerol (IIa)

Following the procedure given in Example Ia, 100 grams (0.216 mole) of hexaglycerol (a polyglycerol containing an average of 6 glycerol units) was added to the reaction apparatus and dried as previously described. Then 1.0 gram of potassium t-butoxide catalyst was added, and the stirred polyglycerol was again vacuum stripped at 150° C. and 10 mm Hg to remove the traces of butanol. Vikolox 12 (Viking Chem. Co.), 80 grams (0.435 mole), an alpha olefin epoxide of dodecene, was then added. A nitrogen blanket was maintained as the flask contents were stirred and held between 150°-160° C. for 6 hours. Analysis for epoxide with pyridine hydrochloride reagent showed 99.4% of the epoxide had reacted.

b. Monosulfation of Dialkoxylated Hexaglycerol

To the reaction versel described in Example Ib was added 83.0 grams (0.100 mole) of the di-1,2-epoxydodecane adduct of hexaglycerol (IIa). Anhydrous methylene chloride (450 grams) was added to solubilize the hexaglycerol derivative. Chlorosulfonic acid (12.2 grams, 0.105 mole) was added dropwise with stirring and external cooling to maintain the temperature below 25° C. Upon completion of the acid addition, the solution was sparged with nitrogen to remove dissolved HCl. The sulfuric acid ester solution of IIa was then added to 10 grams of 17% aqueous ammonium hydroxide dissolved in 550 mL of water. Additional dilute ammonium hydroxide was added to stabilize the pH at 5–6. The methylene chloride was then removed by distillation to yield an aqueous solution of compound II.

EXAMPLE III

Preparation of Trisulfated Tetraalkoxylated Hexaglycerol (III)

a. Synthesis of Tetraalkoxylated Hexaglycerol (IIIa)

Following the procedure given in Example Ia and using the materials described in Example IIa, 100 grams (0.216 mole) of hexaglycerol was added to the reaction apparatus and dried as previously described. Then 1.5 grams of potassium t-butoxide catalyst was added and the stirred polyglycerol was again vacuum stripped to remove the traces of butanol. Vikolox 12, 174.9 grams (0.950 mole), was then added. A nitrogen blanket was maintained as the flask contents were stirred and held between 150°–160° C. for 5 hours. Analysis for epoxide showed 97.5% reaction of the epoxide.

b. Trisulfation of Tetraalkoxylated Hexaglycerol

Following the procedures described in Examples Ib and IIb, 119.8 grams (0.100 mole) of the tetra-1,2-epoxydodecane adduct of hexaglycerol (IIIa) was solubilized with 650 grams of methylene chloride. Chlorosulfonic acid (36.7 grams, 0.315 mole) was reacted with the hexaglycerol derivative in the usual fashion. The acid ester of IIIa was added to 21.3 mL of concentrated ammonium hydroxide previously diluted with one liter of water. Adjustment of pH 5–6 was made with additional dilute ammonium hydroxide. The methylene chloride was then removed by distillation to yield an aqueous solution of compound III.

EXAMPLE IV

The following shampoo composition was prepared.

| Ingredient | % by Weight |
| --- | --- |
| Monosulfated Dialkoxylated Triglycerol | 10.0 |
| Aromox DMC (Akzona Inc.) (a dimethyl-cocoamine oxide) | 10.0 |
| Perfume, preservative, color and water | q.s. to 100 |

The above shampoo was tested for soil removal efficiency (a measure of the cleaning power of the shampoo) and compared with the efficacies of its individual components and two commercial shampoos. The results are tabulated below.

| Shampoo System | % Soil Removal Efficiency at 2.0% Concentration |
| --- | --- |
| Monosulfated Dialkoxylated Triglycerol | 27 |
| Aromox DMC | 28 |
| Shampoo of Example IV | 57 |
| Commercial Baby Shampoo | 27 |
| Commercial Low pH Shampoo | 61 |

The soil removal efficiencies indicate a synergistic effect on admixing the sulfated alkoxylated polyglycerol surfactant and the dimethylcocoamine oxide foam promoter. Evaluation of the shampoo by panelists in a blind comparison test showed the shampoo to be effective in cleaning, lather, rinsing, appearance and feel.

EXAMPLE V

| Ingredient | % by Weight |
| --- | --- |
| Trisulfated Tetraalkoxylated Hexaglycerol | 8.0 |
| Aromox DMC | 8.0 |
| Pluronic F88 (BASF Wyandotte Co.) (a sulfated condensation product of ethylene oxide with a base formed by condensing propylene oxide with propylene glycol) | 10.0 |
| Polyethylene glycol (mol. wt. 6000) distearate | 2.0 |
| Perfume, preservative, color and water | q.s. to 100 |

EXAMPLE VI

| Ingredient | % by Weight |
| --- | --- |
| Tetrasulfated Tetraalkoxylated Hexaglycerol | 14.6 |
| Aromox DMC | 5.4 |
| Pluronic F88 | 10.0 |
| Polyethylene glycol (mol. wt. 6000) distearate | 2.0 |
| Perfume, preservative, color and water | q.s. to 100 |

Each of the above examples, when employed as a hair shampoo, provides the hair with adequate cleaning, manageability and cosmetic appearance and the benefit of an unusually low level of skin and eye irritation.

Having thus described the invention, what is claimed is:

1. A hair shampoo composition in the form of an aqueous solution containing (A) a sulfated alkoxylated polyglycerol prepared by reacting in the presence of an alkali metal alkoxide catalyst (1) a dried polyglycerol having 2 to 15 glycerol units with (2) at least 0.25 mole per mole of glycerol contained in the polyglycerol of an alpha olefin epoxide of the general formula

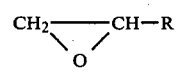

wherein R is an alkyl group containing from 8 to 16 carbon atoms, and then reacting the resulting product with 0.3 to 2.0 moles per mole of alpha olefin epoxide of a sulfating agent and (B) an amine oxide of the general formula

wherein $R_1$ is an alkyl group containing from about 10 to 16 carbon atoms and $R_2$ and $R_3$ are each selected from the group consisting of methyl and ethyl groups.

2. A hair shampoo composition as described in claim 1 in which the polyglycerol has 3 to 8 glycerol units.

3. A hair shampoo composition as described in claim 1 in which the quantity of sulfating agent used in preparing the sulfated alkoxylated polyglycerol is 0.5 to 1.2 moles per mole of alpha olefin epoxide.

4. A hair shampoo composition as described in claim 1 in which the sulfating agent employed in preparing the sulfated alkoxylated polyglycerol is a sulfur trioxide complex.

5. A hair shampoo composition as described in claim 1 in which the sulfated alkoxylated polyglycerol comprises about 5 to 20% by weight of the total composition.

6. A hair shampoo composition as described in claim 1 in which the amine oxide comprises about 5 to 20% by weight of the total composition.

* * * * *